United States Patent
Kitagawa et al.

(10) Patent No.: US 12,360,397 B2
(45) Date of Patent: Jul. 15, 2025

(54) METHOD FOR PRODUCING COATED MEDICAL DEVICE

(71) Applicant: TORAY Industries, Inc., Tokyo (JP)

(72) Inventors: Rumiko Kitagawa, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 18/278,669

(22) PCT Filed: Feb. 4, 2022

(86) PCT No.: PCT/JP2022/004406
§ 371 (c)(1),
(2) Date: Aug. 24, 2023

(87) PCT Pub. No.: WO2022/185833
PCT Pub. Date: Sep. 9, 2022

(65) Prior Publication Data
US 2024/0160043 A1    May 16, 2024

(30) Foreign Application Priority Data
Mar. 2, 2021 (JP) ................. 2021-032264

(51) Int. Cl.
G02C 7/04        (2006.01)
A61L 29/08       (2006.01)

(52) U.S. Cl.
CPC ............. G02C 7/04 (2013.01); A61L 29/085 (2013.01); A61L 2300/404 (2013.01); A61L 2420/02 (2013.01)

(58) Field of Classification Search
CPC .................................. G02C 7/047
See application file for complete search history.

(56) References Cited

U.S. PATENT DOCUMENTS

| | | | | |
|---|---|---|---|---|
| 6,555,225 B1* | 4/2003 | Yoshioka | ............ | A61L 33/0011 427/195 |
| 2008/0039550 A1* | 2/2008 | Miyabayashi | ........... | B01J 13/14 523/200 |
| 2008/0314767 A1 | 12/2008 | Lai et al. | | |
| 2013/0188124 A1* | 7/2013 | Li | ..................... | B29D 11/00038 427/164 |
| 2014/0174957 A1* | 6/2014 | Rogers | .................. | G02B 1/043 53/431 |
| 2015/0366311 A1* | 12/2015 | Maltseva | ............... | B65D 81/22 53/472 |
| 2016/0102213 A1* | 4/2016 | Hayashi | .................. | A61L 29/02 428/522 |
| 2017/0266353 A1* | 9/2017 | Murphy | ................. | A61L 29/106 |
| 2018/0217294 A1* | 8/2018 | Hyuugaji | .............. | C08F 220/58 |
| 2019/0099511 A1* | 4/2019 | Yamashita | ............ | C08F 220/54 |
| 2019/0127541 A1* | 5/2019 | Kamizono | ............... | C08J 7/054 |
| 2020/0385653 A1 | 12/2020 | Sakurai et al. | | |
| 2022/0184908 A1 | 6/2022 | Kitagawa et al. | | |

FOREIGN PATENT DOCUMENTS

| | | |
|---|---|---|
| EP | 0 956 870 A1 | 11/1999 |
| JP | 11-99200 A | 4/1999 |
| JP | 2019-81878 A | 5/2019 |
| WO | WO 2017/018425 A1 | 2/2017 |
| WO | WO 2020/121940 A1 | 6/2020 |
| WO | WO 2020/235275 A1 | 11/2020 |

OTHER PUBLICATIONS

International Search Report (PCT/ISA/210), issued in PCT/JP2022/004406, dated Mar. 22, 2022.
Written Opinion of the International Searching Authority (PCT/ISA/237), issued in PCT/JP2022/004406, dated Mar. 22, 2022.
Extended European Search Report for European Application No. 22762890.6, dated Oct. 30, 2024.

* cited by examiner

*Primary Examiner* — Cachet I Proctor
(74) *Attorney, Agent, or Firm* — Birch, Stewart, Kolasch & Birch, LLP

(57) ABSTRACT

An object of the present invention is to provide a simple method for manufacturing a coated medical device allowed to have not only properties such as sufficient hydrophilicity but also a bacteria adhesion inhibiting capability. The present invention provides a method for manufacturing a coated medical device, including: (A) a contacting step of housing a medical device in a container, and bringing the medical device into contact with a solution a containing a hydrophilic polymer A; and (C) a heating step of heating the container; wherein the hydrophilic polymer A is a polymer containing, as a monomer unit, a compound having a quaternary ammonium cation group; and wherein the pH of the solution a after the heating step is 6.1 to 8.0.

10 Claims, No Drawings

METHOD FOR PRODUCING COATED MEDICAL DEVICE

TECHNICAL FIELD

The present invention relates to a method of manufacturing a coated medical device.

BACKGROUND ART

Medical devices produced using soft materials such as a silicone rubber and hydrogel or medical devices produced using hard materials such as metal and glass have hitherto been used for diverse applications in various fields.

In cases where a medical device is introduced into a living body or attached to the surface of a living body, it becomes important to modify the surface of the medical device for the purpose of enhancing the biocompatibility of the device. If the surface modification not only enhances the biocompatibility but also allows the medical device to have properties such as hydrophilicity, lubricity, and a bacteria adhesion inhibiting capability, users can expect an improvement in feeling of use, a reduction in discomfort, an improvement in symptoms, and the like.

Examples of a known method for modifying the surface of a medical device include a method in which a medical device is heated in a pH 2.0 to 6.0 solution containing a polymer having a hydroxyl group, whereby a coating is formed on the surface to afford good hydrophilicity to the surface of the medical device (Patent Literature 1).

Another known method is a method in which a medical device is autoclaved and sterilized in a pH 6 to 9 solution containing one or more polymers, for example, acid-terminated polyvinylpyrrolidone, to form a coating on the surface, thereby enhancing the attachability of the medical device (Patent Literature 2 to 4).

CITATION LIST

Patent Literature

Patent Literature 1: WO2017/146102
Patent Literature 2: JP2011-512546W
Patent Literature 3: JP2003-535626W
Patent Literature 4: JP5154231

SUMMARY OF INVENTION

Technical Problem

However, in a method disclosed in Patent Literature 1, the pH of the solution after heating is 6.0 or less, and thus, the coated medical device has to be sterilized after being washed with a neutral solution to remove a stimulus against a living body. Furthermore, the method cannot afford a bacteria adhesion inhibiting capability.

In addition, none of the inventions disclosed in Patent Literature 2 to 4 can afford sufficient hydrophilicity or the like to the surface of a medical device, and furthermore, none of the inventions are methods that can afford a bacteria adhesion inhibiting capability to a medical device.

In view of this, an object of the present invention is to provide a simple method for manufacturing a coated medical device allowed to have not only properties such as sufficient hydrophilicity but also a bacteria adhesion inhibiting capability.

Solution to Problem

To achieve the object, the present invention includes: (A) a contacting step of housing a medical device in a container, and bringing the medical device into contact with a solution a containing a hydrophilic polymer A; and (C) a heating step of heating the container; wherein the hydrophilic polymer A is a polymer containing, as a monomer unit, a compound having a quaternary ammonium cation group represented by the following general formula (I).

[Chem. 1]

In the general formula (I), $R^1$ represents an optionally substituted $C_{1-20}$ divalent organic group; and $R^2$ to $R^4$ each independently represent an optionally substituted $C_{1-20}$ alkyl group or an optionally substituted $C_{6-20}$ aryl group.

Provided is a method for manufacturing a coated medical device, wherein the pH of the solution a after the above-described heating step is 6.1 to 8.0.

Advantageous Effects of Invention

According to the present invention, a simple process makes it possible to obtain a coated medical device provided with not only basic properties such as sufficient hydrophilicity demanded for a medical device but also a bacteria adhesion inhibiting capability.

DESCRIPTION OF EMBODIMENTS

A method for manufacturing a coated medical device according to the present invention includes: (A) a contacting step of housing a medical device in a container, and bringing the medical device into contact with a solution a containing a hydrophilic polymer A; and (C) a heating step of heating the container; wherein the hydrophilic polymer A is a polymer containing, as a monomer unit, a compound a1 having a quaternary ammonium cation group represented by the following general formula (I).

[Chem. 2]

In the general formula (I), $R^1$ represents an optionally substituted $C_{1-20}$ divalent organic group; and $R^2$ to $R^4$ each independently represent an optionally substituted $C_{1-20}$ alkyl group or an optionally substituted $C_{6-20}$ aryl group.

The pH of the solution a after the heating step is characterized by being 6.1 to 8.0.

Examples of the medical device to be used in a method for manufacturing a coated medical device according to the present invention include an ophthalmic lens, a dermal covering material, a wound dressing material, a skin protection material, a skin medicine carrier, an infusion tube, a gas delivery tube, a drainage tube, a blood circuit, a covering tube, a catheter, a stent, a sheath, a biosensor chip, an artificial heart and lung, or an endoscopic covering material. Here, examples of the ophthalmic lens include a contact lens, an intraocular lens, an artificial cornea, a corneal inlay, a corneal onlay, and an eyeglass lens.

A material constituting the medical device may be any one of a hydrous material and a low water content material. Examples of the hydrous material include a hydrogel or a silicone hydrogel. In cases where the medical device is a contact lens, a hydrogel is preferable because the hydrogel can form a durable surface layer having a high lipid adhesion inhibiting capability, and exhibiting excellent hydrophilicity and lubricity, and sustain the effect during long-time attachment. Examples of the low water content material include a low water content soft material and a low water content hard material. In this regard, the low water content material refers to a material the moisture content of which is 10% by mass or less.

Hereinafter, United States Adopted Names (USAN) is used to express the name of a hydrogel or a silicone hydrogel in some cases. In the USAN, variations of a material are expressed with a symbol such as A, B, or C added at the end in some cases, and in the present specification, a name having no symbol added at the end represents all the variations. For example, a name expressed simply as "ocufilcon" represents all variations of ocufilcon, such as "ocufilcon A", "ocufilcon B", "ocufilcon C", "ocufilcon D", "ocufilcon E", and "ocufilcon F".

Examples of the hydrogel include tefilcon, tetrafilcon, hefilcon, mafilcon, polymacon, hioxifilcon, alfafilcon, omafilcon, hixoifilcon, nelfilcon, nesofilcon, hilafilcon, acofilcon, deltafilcon, etafilcon, focofilcon, ocufilcon, phemfilcon, methafilcon, and vilfilcon.

A medical device that is a contact lens composed of a hydrogel belongs to Group 1 to Group 4 prescribed in the classification of contact lenses by the Food and Drug Administration (FDA). Group 2 or Group 4, which exhibits a good bacteria adhesion inhibiting capability and exhibits hydrophilicity, is preferable, and Group 4 is more preferable.

Examples of a nonionic hydrogel which belongs to Group 1 and the moisture content of which is less than 50% by mass include tefilcon, tetrafilcon, hefilcon, mafilcon, polymacon, and hioxifilcon.

Examples of a nonionic hydrogel which belongs to Group 2 and the moisture content of which is 50% by mass or more include alfafilcon, omafilcon, hioxifilcon, nelfilcon, nesofilcon, hilafilcon, and acofilcon. Omafilcon, hioxifilcon, nelfilcon, or nesofilcon, which each exhibits a good bacteria adhesion inhibiting capability and exhibits good hydrophilicity, is preferable. Omafilcon or hioxifilcon is more preferable. Omafilcon is still more preferable.

Examples of an ionic hydrogel which belongs to Group 3 and the moisture content of which is less than 50% by mass include deltafilcon.

Examples of an ionic hydrogel which belongs to Group 4 and the moisture content of which is 50% by mass or more include etafilcon, focofilcon, ocufilcon, phemfilcon, methafilcon, and vilfilcon. Etafilcon, focofilcon, ocufilcon, or phemfilcon, which each exhibits a good bacteria adhesion inhibiting capability and exhibits good hydrophilicity, is preferable. Etafilcon or ocufilcon is more preferable, and etafilcon is still more preferable.

A medical device that is a contact lens composed of a silicone hydrogel preferably belongs to Group 5 prescribed in the classification of contact lenses by the Food and Drug Administration (FDA).

A silicone hydrogel belonging to Group 5 is preferably a polymer having a silicon atom in the main chain and/or side chain, and having hydrophilicity, and examples thereof include a copolymer of a monomer having a siloxane bond and a hydrophilic monomer. Examples of such a copolymer include lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon. Lotrafilcon, galyfilcon, narafilcon, senofilcon, comfilcon, enfilcon, stenfilcon, somofilcon, delefilcon, balafilcon, or samfilcon, which each exhibits not only a bacteria adhesion inhibiting capability but also good hydrophilicity and antifouling properties, is preferable. Lotrafilcon, narafilcon, senofilcon, comfilcon, or enfilcon is more preferable. Narafilcon, senofilcon, or comfilcon is still more preferable.

In cases where the medical device is a contact lens, the low water content soft material or the low water content hard material is preferably a silicon atom-containing material that exhibits a high oxygen permeability, and is capable of supplying sufficient oxygen to the cornea.

The low water content hard material is preferably a low water content hard material that belongs to the classification of contact lens prescribed by the Food and Drug Administration (FDA).

The low water content hard material is preferably a polymer having, in the main chain and/or a side chain, a silicon atom such as in a siloxane bond, more preferably a material having a high oxygen permeability, for example, tris(trimethylsilyloxy)silyl]propyl methacrylate, polydimethyl siloxane having a double bond at both ends, a homopolymer containing a silicone-containing acrylate, silicone-containing methacrylate, or the like, or a copolymer of such a polymer and another monomer.

Specifically, the above-described low water content hard material is preferably selected from the group consisting of neofocon, pasifocon, telefocon, silafocon, paflufocon, petrafocon, and fluorofocon. Among these, neofocon, pasifocon, telefocon, or silafocon is more preferable from the viewpoint of exhibiting a good bacteria adhesion inhibiting capability and exhibiting antifouling properties. Neofocon, pasifocon, or telefocon is still more preferable. Neofocon is particularly preferable.

In cases where the medical device is other than a contact lens, the low water content hard material is preferably polyethylene, polypropylene, polysulfone, polyetherimide, polystyrene, polymethyl methacrylate, polyamide, polyester, epoxy resin, polyurethane, or polyvinyl chloride. Among these, polysulfone, polystyrene, polymethyl methacrylate, polyurethane, or polyamide is more preferable from the viewpoint of exhibiting a good bacteria adhesion inhibiting capability and exhibiting antifouling properties. Polymethyl methacrylate is still more preferable.

Examples of the low water content soft material include: a material disclosed in WO2013/024799, and having a moisture content of 10% by mass or less, an elastic modulus of 100 to 2,000 kPa, and a tensile elongation of 50 to 3,000%; and elastofilcon.

The manufacturing method according to the present invention makes it possible that, whether the medical device is hydrous or has a low water content, the surface of the medical device has a suitable bacteria adhesion inhibiting capability. In order to afford a suitable bacteria adhesion inhibiting capability, the moisture content of the medical device is preferably 0.0001% by mass or more, more preferably 0.001% by mass or more. In addition, the moisture content of the medical device is preferably 80% by mass or less, more preferably 70% by mass or less, still more preferably 60% by mass or less.

In order that a medical device that is a contact lens can make it easy to ensure the movement of the lens in an eye, the moisture content of the medical device is preferably 15% by mass or more, more preferably 20% by mass or more.

The hydrophilic polymer A is hydrophilic. Here, being "hydrophilic" means that the polymer in an amount of 0.0001 part by mass or more is soluble in 100 parts by mass of water or a liquid mixture of 100 parts by mass of water and 100 parts by mass of tert-butanol at room temperature (20 to 23° C.). The hydrophilic polymer is preferably soluble in an amount of 0.01 part by mass or more, more preferably 0.1 part by mass or more, still more preferably 1 part by mass or more.

The hydrophilic polymer A is a polymer containing, as a monomer unit, a compound a1 having a quaternary ammonium cation group represented by the following general formula (I).

[Chem. 3]

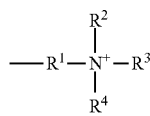
(I)

In the general formula (I), $R^1$ represents an optionally substituted $C_{1-20}$ divalent organic group; and $R^2$ to $R^4$ each independently represent an optionally substituted $C_{1-20}$ alkyl group or an optionally substituted $C_{6-20}$ aryl group.

Examples of $R^1$ include an alkylene group such as a methylene group, ethylene group, propylene group, butylene group, pentylene group, octylene group, decylene group, dodecylene group, or octadecylene group; or an arylene group such as a phenylene group or a naphthylene group. These alkylene groups and arylene groups may be linear or branched. The carbon number of $R^1$ is preferably 1 to 16, more preferably 1 to 10, so that both the compatibility with water and a bacteria adhesion inhibiting capability can be suitable.

In cases where $R^1$ has a substituent, examples of the substituent include a hydroxyl group, carboxyl group, sulfonic group, phosphoric acid group, ester group, ether group, or amide group. To enhance the compatibility with water, a hydroxyl group, ester group, ether group, or amide group is preferable. To enhance an obtainable bacteria adhesion inhibiting capability, a hydroxyl group or an ether group is preferable.

More suitable examples of $R^1$ include an ethylene group, propylene group, butylene group, and organic group represented by the following formulae (a1) to (a4). An ethylene group, propylene group, or organic group represented by any one of the following general formulae (a1) to (a4) is preferable. An ethylene group, propylene group, or organic group represented by the following general formula (a2) is more preferable.

[Chem. 4]

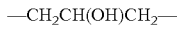 (a1)

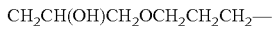 (a2)

 (a3)

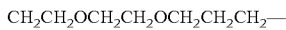 (a4)

$R^2$ to $R^4$ are each independently, for example, an alkyl group such as a methyl group, ethyl group, propyl group, butyl group, pentyl group, octyl group, decyl group, dodecyl group, or octadecyl group; or an aryl group such as a phenyl group or a naphthyl group. These alkyl groups and aryl groups may be linear or branched. The carbon number of any one of $R^2$ to $R^4$ that are alkyl groups is preferably 1 to 16, more preferably 1 to 10, so that both the compatibility with water and a bacteria adhesion inhibiting capability can be suitable. The carbon number of any one of $R^2$ to $R^4$ that are aryl groups is preferably 6 to 18, more preferably 6 to 12, from the viewpoint of both the compatibility with water and easy polymerization with another compound.

A quaternary ammonium cation group represented by the general formula (I) usually is accompanied by a counter anion. Examples of a suitable counter anion include; a halogenide ion such as a chloride ion, bromide ion, or iodide ion; a hydroxide ion; a carboxylate ion; a sulfonate ion; a sulfate ion; a nitrate ion; a carbonate ion; a phosphate ion; a borate ion; a hypochlorite ion; and the like.

From a high-polymerizability viewpoint, a compound a1 having a quaternary ammonium cation group represented by the general formula (I) is preferably a compound having a polymerizable carbon-to-carbon unsaturated bond other than a quaternary ammonium cation group represented by the general formula (I). Examples of the compound having a polymerizable carbon-to-carbon unsaturated bond include a compound having a vinyl group, compound having an allyl group, maleic acid ester compound, maleimide compound, itaconic acid ester compound, methacrylic acid ester compound, acrylic acid ester compound, methacrylamide compound, or acrylamide compound. A methacrylic acid ester compound, acrylic acid ester compound, methacrylamide compound, or acrylamide compound is preferable.

It is preferable that the hydrophilic polymer A further contains, as a monomer unit, a compound having a structure represented by the following general formula (II), because the resulting coated medical device exhibits good hydrophilicity.

[Chem. 5]

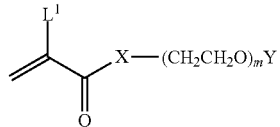
(II)

In the general formula (II), $L^1$ represents a hydrogen atom or a methyl group; X represents an oxygen atom or $NA^2$, wherein $A^2$ represents a hydrogen atom or an alkyl group; m represents an integer of 1 to 30; and Y represents a hydrogen atom or an alkyl group.

$A^2$ that is an alkyl group may be linear or branched, and is preferably a $C_{1-10}$ alkyl group. Examples of $A^2$ include a methyl group, ethyl group, propyl group, 2-propyl group, butyl group, 2-butyl group, tert-butyl group, pentyl group, 2-pentyl group, 3-pentyl group, hexyl group, heptyl group, or octyl group.

m is preferably 3 to 30 from the viewpoint of suitable hydrophilicity and easy polymerization. The lower limit of m is more preferably 4, still more preferably 7, particularly preferably 9. The upper limit of m is more preferably 25, still more preferably 23, particularly preferably 13.

Y is preferably an alkyl group, more preferably a $C_{1-5}$ alkyl group, still more preferably a methyl group, ethyl group, propyl group, isopropyl group, or butyl group, particularly preferably a methyl group or an ethyl group, most preferably a methyl group, from the viewpoint of easy formation of a coating layer.

In cases where the hydrophilic polymer A contains, as a monomer unit, the compound a2 having a structure represented by the general formula (II), the copolymerization ratio of the compound a1 having a quaternary ammonium cation group represented by the general formula (I) to the compound a2 represented by the general formula (II) is preferably in the range of from 1/99 to 99/1 by mass to make it easier to exhibit a function such as a bacteria adhesion inhibiting capability or durable hydrophilicity. That is, with respect to 100% by mass of the whole hydrophilic polymer A, the content of the compound a1 is preferably 1% by mass or more and preferably 99% by mass or less. With respect to 100% by mass of the whole hydrophilic polymer A, the ratio of the compound a2 is preferably 1% by mass or more and preferably 99% by mass or less.

A compound that can be used as each of the compound a1 and the compound a2 is a single monomer or a mixture of a plurality of different monomers having different structures.

With respect to 100% by mass of the whole hydrophilic polymer A, the content of the compound a1 is more preferably 2% by mass or more, still more preferably 5% by mass or more, particularly preferably 10% by mass or more. In addition, the content of the compound a1 is more preferably 90% by mass or less, still more preferably 85% by mass or less, particularly preferably 80% by mass or less. With respect to 100% by mass of the whole hydrophilic polymer A, the content of the compound a2 is more preferably 10% by mass or more, still more preferably 15% by mass or more, particularly preferably 20% by mass or more. In addition, the content of the compound a2 is more preferably 90% by mass or less, still more preferably 80% by mass or less, particularly preferably 70% by mass or less.

The hydrophilic polymer A may contain a monomer unit other than the compound a1 and the compound a2. The hydrophilic polymer A that contains, as a monomer unit, a compound having an amide group has an amide group. In cases where the hydrophilic polymer A has an amide group, the hydrophilic polymer A exhibits a suitable viscosity when dissolved in water, thus can form a not only hydrophilic but also lubricous surface, and hence, the hydrophilic polymer A preferably has an amide group.

The compound having an amide group is preferably a compound having an acrylamide group or a methacrylamide group, or an N-vinyl carboxylic amide (encompassing a cyclic compound) from the viewpoint of easy polymerization. However, a compound that satisfies the general formula (II) is excluded from the compounds having an amide group as described here.

Specific examples include N-vinylpyrrolidone, N-vinylcaprolactam, N-vinylacetamide, N-methyl-N-vinylacetamide, N-vinylformamide, N,N-dimethylacrylamide, N-isopropylacrylamide, N-methylacrylamide, N-ethylacrylamide, N-butylacrylamide, N-tert-butylacrylamide, N-hydroxymethylacrylamide, N-methoxymethylacrylamide, N-ethoxymethylacrylamide, N-propoxymethylacrylamide, N-isopropoxymethylacrylamide, N-(2-hydroxyethyl)acrylamide, N-butoxymethylacrylamide, N-isobutoxymethylacrylamide, N-hydroxymethylmethacrylamide, N-methoxymethylmethacrylamide, N-ethoxymethylmethacrylamide, N-propoxymethylmethacrylamide, N-butoxymethylmethacrylamide, N-isobutoxymethylmethacrylamide, acryloyl morpholine, and acrylamide. For the purpose of enhancing the lubricity, N-vinylpyrrolidone, N-isopropylacrylamide, or N,N-dimethylacrylamide is preferable. N-isopropylacrylamide, or N,N-dimethylacrylamide is more preferable, and N,N-dimethylacrylamide is still more preferable.

In a case where the hydrophilic polymer A contains, as a monomer unit, a compound having an amide group, the content of (i) the compound a1 to the total of (i) the compound a1, (ii) the compound a2, and (iii) the compound having an amide group, which are monomer units of the hydrophilic polymer A, is preferably 3% by mass or more, more preferably 5% by mass or more, still more preferably 10% by mass or more, still more preferably 20% by mass or more, to allow the easier exhibition of not only a bacteria adhesion inhibiting capability but also functions such as lubricity and antifouling properties for body fluids. In addition, the content of (i) the compound a1 is preferably 90% by mass or less, more preferably 80% by mass or less, still more preferably 70% by mass or less, particularly preferably 50% by mass or less. The content of (ii) the compound a2 is preferably 5% by mass or more, more preferably 10% by mass or more, still more preferably 30% by mass or more, particularly preferably 40% by mass or more. In addition, the content of (ii) the compound a2 is preferably 95% by mass or less, more preferably 85% by mass or less, still more preferably 80% by mass or less. The content of (iii) the compound having an amide group is preferably 3% by mass or more, more preferably 5% by mass or more, still more preferably 10% by mass or more. In addition, the content of (iii) the compound having an amide group is preferably 90% by mass or less, more preferably 80% by mass or less, still more preferably 70% by mass or less, particularly preferably 60% by mass or less.

The hydrophilic polymer A may further contain, as a monomer unit, a compound other than above-described. Examples of the another compound that the hydrophilic polymer A contains as a monomer unit include glycerol acrylate, glycerol methacrylate, N-(4-hydroxyphenyl)maleimide, hydroxystyrene, and a vinyl alcohol (a vinyl carboxylate ester as a precursor). To enhance the antifouling properties for body fluids, glycerol acrylate, glycerol methacrylate, or a vinyl alcohol is preferable, and glycerol acrylate or glycerol methacrylate is more preferable. In addition, it is also possible to use, as the another compound, a compound having functions such as hydrophilicity, antibacterial properties, antifouling properties, and medicinal effects.

A method for manufacturing a coated medical device according to the present invention includes (A) a contacting step of housing a medical device in a container, and bringing the medical device into contact with a solution a containing a hydrophilic polymer A.

To enhance the adsorptive force of the hydrophilic polymer A on the surface of the medical device, and provide the medical device with a sufficient bacteria adhesion inhibiting capability, the weight-average molecular weight of the hydrophilic polymer A is preferably 2,000 to 1,500,000. The weight-average molecular weight is more preferably 5,000 or more, still more preferably 10,000 or more, particularly preferably 100,000 or more. In addition, the weight-average molecular weight is more preferably 1,200,000 or less, still more preferably 1,000,000 or less, particularly preferably 900,000 or less. Here, the weight-average molecular weight is a weight-average molecular weight in terms of polyethylene glycol, as measured by a gel permeation chromatography method in which an aqueous solvent is used as an eluent.

The concentration of the hydrophilic polymer A in the solution a containing the hydrophilic polymer A is preferably in the range of from 0.0001 to 30% by mass to adjust the viscosity of the solution a suitably. The concentration of the hydrophilic polymer A is more preferably 0.001% by mass or more, still more preferably 0.005% by mass or more. In addition, the concentration of the hydrophilic polymer A is more preferably 10.0% by mass or less, still more preferably 5.0% by mass or less, still more preferably 1.0% by mass or less, particularly preferably 0.5% by mass or less.

A solvent of the solution a containing the hydrophilic polymer A is preferably a water-soluble organic solvent or water, or a solvent mixture thereof from the viewpoint of easy handling. A solvent mixture of water and a water-soluble organic solvent, or water is more preferable, and water is still more preferable. The water-soluble organic solvent is preferably a water-soluble alcohol, more preferably a water-soluble alcohol having 6 or less carbon atoms, still more preferably a water-soluble alcohol having 5 or less carbon atoms. The solution a may further contain a buffering agent or another additive.

Examples of the buffering agent to be contained in the solution a include boric acid, borates (for example, sodium borate), citric acid, citrates (for example, potassium citrate), bicarbonate (for example, sodium bicarbonate), phosphate buffer solution (for example, $Na_2HPO_4$, $NaH_2PO_4$, and $KH_2PO_4$), TRIS (tris(hydroxymethyl)aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid), BES (N,N-bis(2-hydroxyethyl)-2-aminoethanesulfonic acid), HEPES (4-(2-hydroxyethyl)-1-piperazineethanesulfonic acid), MES (2-(N-morpholino) ethanesulfonic acid), MOPS (3-[N-morpholino-propanesulfonic acid), PIPES (piperazine-N,N'-bis(2-ethanesulfonic acid)), TES (N-[tris(hydroxymethyl)methyl]-2-aminoethanesulfonic acid), and salts thereof. The content of the buffering agent in the solution a can be suitably adjusted to achieve a desired pH, and usually, the content is preferably 0.001 to 2.000% by mass. The content of the buffering agent is more preferably 0.010% by mass or more, still more preferably 0.050% by mass or more. In addition, the content of the buffering agent is more preferably 1.000% by mass or less, still more preferably 0.300% by mass or less.

The pH of the buffering agent solution to be used for adjustment of the solution a is preferably within a physiologically acceptable range of from 6.3 to 7.8. The pH of the buffering agent solution is more preferably 6.5 or more, still more preferably 6.8 or more. In addition, the pH of the buffering agent solution is more preferably 7.6 or less, still more preferably 7.4 or less.

In cases where the medical device is an ophthalmic lens, examples of the container for housing the medical device in the contacting step include a vial or blister container to be used for packaging an ophthalmic lens. A blister container is usually composed of: a plastic base portion surrounded by a flat flange standing in a warped manner around the brim of the cavity of the container; and a soft cover sheet bonded to the flat flange and configured to hermetically seal the cavity.

Examples of the material for the plastic base portion include fluorine resins, polyamides, polyacrylate, polyethylene, nylons, olefin copolymers (for example, a polypropylene polyethylene copolymer), polyethylene terephthalate, polyvinyl chloride, amorphous polyolefins, polycarbonate, polysulfone, polybutylene terephthalate, polypropylene, polymethyl pentene, polyesters, rubbers, and urethane.

Examples of the soft cover sheet include a laminate material such as a polypropylene sheet coated with an aluminum foil.

A method for manufacturing a coated medical device according to the present invention includes a heating step of heating (C) the above-described container.

Examples of the above-described heating method include a heating method (with hot air), high-pressure steam sterilization method, dry heat sterilization method, burning sterilization method, boiling sterilization method, free-flowing steam sterilization method, electromagnetic wave (γ-ray, microwave, or the like) irradiation, ethylene oxide gas sterilization method (EOG sterilization method), or ultraviolet sterilization method. A high-pressure steam sterilization method is preferable from the viewpoint of the capability to afford sufficient hydrophilicity to the medical device and of the low manufacturing cost. Autoclave sterilization performed using a device that is an autoclave is more preferable.

The heating temperature is preferably 80 to 200° C. to provide the medical device with a sufficient bacteria adhesion inhibiting capability, and simultaneously to cause no influence on the strength of the resulting coated medical device itself. The heating temperature is more preferably 90° C. or more, still more preferably 105° C. or more, still more preferably 110° C. or more, still more preferably 115° C. or more, particularly preferably 121° C. or more. In addition, the heating temperature is more preferably 180° C. or less, still more preferably 170° C. or less, particularly preferably 150° C. or less.

In addition, the heating time is preferably 1 to 600 minutes for the same reason as with the heating temperature. The heating time is more preferably 2 minutes or more, still more preferably 5 minutes or more, particularly preferably 10 minutes or more. In addition, the heating time is more preferably 400 minutes or less, still more preferably 300 minutes or less, particularly preferably 100 minutes or less.

A method for manufacturing a coated medical device according to the present invention preferably further includes (B) a hermetically sealing step in which the container with the medical device housed therein is hermetically sealed after the contacting step and before the heating step. Hermetically sealing the container with the medical device housed therein, followed by performing the heating step, provides the surface of the medical device with a bacteria adhesion inhibiting capability, simultaneously sterilizes the resulting coated medical device, makes it possible to maintain the sterilized state, and hence, has an industrially important meaning from the viewpoint of reducing the manufacturing processes. That is, it is preferable in a method for manufacturing a coated medical device according to the present invention that the medical device is sterilized by the heating step to simplify the manufacturing processes. Here, examples of a means for hermetically sealing the container include a means for hermetically sealing the container using a vial with a cap or a blister container as a container for housing the medical device. In addition, in cases where the medical device is a contact lens, one example is a means for hermetically sealing the container using, as a container for housing the medical device, a common lens case accessory to care items for a contact lens.

After the above-described heating step, the obtained coated medical device obtained may be further subjected to other treatments. Examples of such other treatments include: a method in which the coated medical device is subjected to a similar heating treatment with a buffering agent solution containing no hydrophilic polymer: radiation of an ion beam, electron beam, positron beam, X-rays, γ-rays, neutron rays, or the like; an LbL treatment (a Layer by Layer treatment, for example, a treatment described in WO2013/024800) in which different polymer materials having opposite charges are alternately applied layer by layer; or a crosslinking treatment with a metal ion or a chemical crosslinking treatment (for example, a treatment described in JP2014-533381W).

In addition, before the above-described contacting step and the above-described heating step, the surface of the medical device may be pretreated. Examples of the pretreatment include a hydrolysis treatment with an acid such as polyacrylic acid, or an alkali such as sodium hydroxide.

For a method for manufacturing a coated medical device according to the present invention, it is required that the pH of the solution a after the heating step be 6.1 to 8.0. Having the pH within this range eliminates the necessity to wash, with a neutral solution, the resulting coated medical device after the heating step, and has an industrially important meaning from the viewpoint of reducing the manufacturing processes. In some of the cases where the heating step is followed by washing with a neutral solution, the resulting coated medical device needs to be sterilized again. The pH of the solution a after the heating step is preferably 6.5 or more, more preferably 6.6 or more, still more preferably 6.7 or more, particularly preferably 6.8 or more. In addition, the pH is preferably 7.9 or less, more preferably 7.8 or less, still more preferably 7.6 or less.

The pH of the solution a before the heating step is preferably 6.1 to 8.0. Here, the pH of the solution a before the heating step refers to a pH value measured after the solution a is prepared, and then stirred with a rotor at room temperature (20 to 23° C.) for 30 minutes to thereby make the solution uniform.

The pH of the solution a can be measured using a pH meter (for example, a pH meter Eutech pH 2700 (manufactured by Eutech Instruments)). The pH value is rounded off to one decimal place.

There is preferably no covalent bond present between the coating layer of the resulting coated medical device, that is, the hydrophilic polymer layer, and the medical device. Having no covalent bond makes it possible to manufacture the coated medical device in a simpler step independently of whether the medical device is a hydrous material or a low water content material. Here, having no covalent bond refers to having no chemically reactive group between the hydrophilic polymer layer and the medical device or no group generated by the reaction of the reactive group. Having no chemically reactive group or no group generated by the reaction of the reactive group can be verified by elemental analysis such as electron energy-loss spectroscopy, energy dispersive X-ray spectrometry, or time-of-flight secondary ion mass spectrometry, or by a composition analysis means. Examples of the chemically reactive group include an azetidinium group, epoxy group, isocyanate group, aziridine group, and azlactone group.

The thickness of the hydrophilic polymer layer is preferably 1 to 99 nm, as observed in a cross section vertical to the longitudinal direction of the coated medical device in a frozen state, using a transmission electron microscope. Having the thickness of the hydrophilic polymer layer within this range makes it easier to exhibit functions such as hydrophilicity and lubricity. The thickness of the hydrophilic polymer layer is more preferably 5 nm or more, still more preferably 10 nm or more. In addition, the thickness of the hydrophilic polymer layer is more preferably 95 nm or less, still more preferably 90 nm or less, still more preferably 85 nm or less, still more preferably 50 nm or less, still more preferably 40 nm or less, still more preferably 30 nm or less, still more preferably 20 nm or less, particularly preferably 15 nm or less. In cases where the coated medical device is an ophthalmic lens, the hydrophilic polymer layer having a thickness of less than 100 nm prevents the refraction of light for focusing on the retina from being disturbed, and is less prone to cause poor visibility.

The coating layer of the resulting coated medical device may exist only on a part of the surface of the medical device, may exist on the whole of only one of the surface and the rear face, or may exist on all of the faces.

In addition, the resulting coated medical device, at least a part of the hydrophilic polymer layer and the medical device preferably exist in a mixed state to achieve firmer coating. Here, the state in which the hydrophilic polymer layer and the medical device are mixed refers to a state in which an element derived from the medical device is detected in the hydrophilic polymer layer. The state can be verified by observing a cross section of the coated medical device by elemental analysis such as scanning transmission electron microscopy, electron energy-loss spectroscopy, energy dispersive X-ray spectroscopy, or time-of-flight secondary ion mass spectrometry, or by a composition analysis means.

Owing to allowing the hydrophilic polymer to be firmly bonded to the surface of the medical device, it is preferable to have a mixed layer in the surface of the medical device, in which mixed layer at least a part of the hydrophilic polymer layer and the medical device are mixed. In cases where the mixed layer exists, it is preferable that a two-layer structure composed of the mixed layer and a single layer made only of a hydrophilic polymer is observed. The thickness of the mixed layer can be measured, in the same manner as the above-described thickness of the hydrophilic polymer layer, by observing a cross section vertical to the longitudinal direction of the coated medical device in a frozen state, using a transmission electron microscope. To firmly bond the hydrophilic polymer to the surface of the medical device, the thickness of the mixed layer is preferably 3% or more, more preferably 5% or more, still more preferably 10% or more, with respect to the total thickness of the mixed layer and the single layer. In addition, for the hydrophilicity possessed by the hydrophilic polymer to be sufficiently exhibited, the thickness of the mixed layer is preferably 98% or less, more preferably 95% or less, still more preferably 90% or less, particularly preferably 80% or less, with respect to the total thickness of the mixed layer and the single layer.

In addition to the mixed layer on the surface of the medical device, the mixed portion is preferably observed. As used herein, the "mixed portion" refers to a site having no layer structure, in which site the hydrophilic polymer and the medical device are mixed. That is, that the "mixed portion is observed" refers to a state in which an element derived from the medical device is detected in a portion other than the mixed layer in the hydrophilic polymer layer. The thickness of the mixed portion is preferably 3% or more, more preferably 5% or more, still more preferably 10% or more, with respect to the total thickness of the mixed layer and the mixed portion. In addition, for the hydrophilicity possessed by the hydrophilic polymer to be sufficiently exhibited, the thickness of the mixed portion is preferably 98% or less, more preferably 95% or less, still more preferably 90% or less, particularly preferably 80% or less, with respect to the total thickness of the mixed layer and the mixed portion.

In cases where the resulting coated medical device is an ophthalmic lens or the like, the liquid film retention time on the surface of the coated medical device is preferably longer from the viewpoint of not only preventing attachment to the cornea of a wearer but also making it less likely to feel dry and making it possible to maintain satisfactory comfort for a long time.

Here, the liquid film retention time on the surface of the coated medical device refers to a time during which a liquid film on the surface is retained without being broken, as the coated medical device is stationarily immersed in a solution at room temperature (20 to 23° C.), pulled up from the solution, and retained in the air in such a manner that the longitudinal direction of the device is the gravitational direction. In cases where a test piece is in the shape of a spherical crown such as a contact lens, the test piece is retained in such a manner that the diametric direction of a circle formed by the brim portion of the spherical crown is the gravitational direction. The expression "the liquid film being broken" refers to a phenomenon in which part of the solution covering the surface of the coated medical device is repelled, leaving the surface of the coated medical device no longer covered wholly with the liquid film. The liquid film retention time is preferably 300 seconds or less, more preferably 200 seconds or less, because the liquid film retention time, if too long, causes moisture to be more easily evaporated from the surface of the coated medical device, thus causing the hydrophilic effect to be low.

In cases where the coated medical device is an ophthalmic lens or the like, the contact angle of a droplet on the surface of the coated medical device is preferably smaller from the viewpoint of not only preventing attachment to the cornea of a wearer but also making it less likely to feel dry and making it possible to maintain satisfactory comfort for a long time. A method for measuring the contact angle of a droplet will be described later. In cases where the medical device is a material having a silicon atom, the contact angle of a droplet is preferably 80° or less, preferably 70° or less, more preferably 65° or less.

In cases where the medical device is a material having no silicon atom, the contact angle of a droplet is preferably 70° or less, more preferably 60° or less, still more preferably 55° or less.

In cases where the resulting coated medical device is a coated medical device that is, for example, inserted into a living body when used, the surface of the coated medical device preferably has excellent lubricity. The coefficient of friction, as an indicator that represents lubricity, is preferably 0.500 or less, more preferably 0.200 or less, still more preferably 0.100 or less, still more preferably 0.080 or less. On the other hand, the lubricity, if extremely high, makes it difficult in some cases to handle the coated medical device, and thus, the coefficient of friction is preferably 0.001 or more, more preferably 0.002 or more. A method for measuring the coefficient of friction will be described later.

In cases where the resulting coated medical device is a soft medical device such as an ophthalmic lens, the tensile elastic modulus is preferably 10.00 MPa or less, more preferably 5.00 MPa or less, still more preferably 3.00 MPa or less, still more preferably 2.00 MPa or less, still more preferably 1.00 MPa or less, particularly preferably 0.60 MPa or less, to enhance the comfort. On the other hand, for easier handling, the tensile elastic modulus of the coated medical device is preferably 0.01 MPa or more, more preferably 0.10 MPa or more, still more preferably 0.20 MPa or more, particularly preferably 0.25 MPa or more. In addition, the rate of change in the tensile elastic modulus of the medical device between before and after the heating step, that is, between before and after the coating is preferably ±15.00% or less, more preferably ±13.00% or less, still more preferably ±10.00% or less, to inhibit deformation and the risk of poor feeling of use. A method for measuring the tensile elastic modulus will be described later.

The amount of lipid adhesion on the resulting coated medical device is preferably smaller to enhance the feeling of use, and decrease the risk of bacterial propagation. A method for measuring the amount of lipid adhesion will be described later.

In cases where the resulting coated medical device is an ophthalmic lens, the rate of change in the moisture content of the medical device between before and after the coating is preferably 10% by mass or less, more preferably 8% by mass or less, still more preferably 6% by mass or less, to prevent poor visibility and deformation that are induced by distortion of the refractive index on account of an increase in the moisture content. A method for measuring the moisture content will be described later.

In cases where the resulting coated medical device is an ophthalmic lens, the rate of change in the size of the medical device between before and after the coating is preferably ±5.00% or less, more preferably ±4.00% or less, still more preferably ±3.00% or less, to prevent the cornea from being damaged owing to the deformation.

EXAMPLES

The present invention will be described more specifically by way of Examples and the like, but the present invention is not limited to these Examples. First, analytical methods and evaluation methods in Examples and the like will be shown.

<Hydrophilicity (Liquid Film Retention Time)>

After the heating step, a coated medical device (or medical device) left to stand until cooled to room temperature (20 to 23° C.) was pulled up from a solution in a container, and retained in the air in such a manner that the longitudinal direction of the device was the gravitational direction. The time from the point of time when the device started being retained in the air to the time when part of the liquid film covering the surface of the device was broken was measured through visual observation, and the average of the N=3 values was rated on the following criteria. The maximum of the measurement values was set at 120 seconds.

A: the liquid film on the surface was retained for 20 seconds or more.

B: the liquid film on the surface was broken in 15 seconds or more and less than seconds.

C: the liquid film on the surface was broken in 10 seconds or more and less than seconds.

D: the liquid film on the surface was broken in 1 second or more and less than seconds.

E: the liquid film on the surface was broken in less than 1 second.

<Hydrophilicity after 24-Hour Immersion in New Phosphate Buffer Solution (PBS) (Liquid Film Retention Time after 24 Hours)>

To remove the influence of the hydrophilic polymer not sufficiently adsorbed on the surface of the medical device, the coated medical device or the medical device after the heating step was left to stand in 4 mL of a new phosphate buffer solution in a glass vial at room temperature (20 to 23° C.) for 24 hours. Then, the coated medical device or the medical device pulled up from the phosphate buffer solution in the glass vial was used as a sample (hereinafter referred to as the "sample 5") for evaluation in the same manner as in the above-described "Hydrophilicity".

<Contact Angle of Droplet>

A contact angle meter (a liquid droplet method) Drop master DM500 (manufactured by Kyowa Interface Science Co., Ltd.) was used for the measurement. Specifically, water was wiped off the surface of the coated medical device (or the medical device), which was then placed on a hemispherical polypropylene having a diameter of 14 mm. The resulting piece was used as a sample. The sample was set in the contact angle meter, a phosphate buffer solution was dropped onto the sample, and the contact angle of the droplet was measured. The amount of the phosphate buffer solution dropped was 20 μL. The average of the N=3 values was regarded as the contact angle of the droplet.

<Contact Angle of Droplet after 24-Hour Immersion in New Phosphate Buffer Solution (PBS) (Contact Angle X of Droplet)>

The Sample S was Provided Separately and Evaluated in the Same Manner as in the above-described "Contact Angle of Droplet".

<Contact Angle of Droplet after 24-Hour Immersion in New Phosphate Buffer Solution (PBS) and Additional 1-Minute Scrubbing (Contact Angle Y of Droplet)>

The sample S was provided separately, scrubbed between the fingers (the thumb and the index finger) for 1 minute, and evaluated in the same manner as in the above-described "Contact Angle of Droplet".

<Evaluation of Bacteria Adhesion Inhibiting Capability>

Three coated medical devices (or medical devices) left to stand until cooled to room temperature (20 to 23° C.) after the heating step were provided. Pseudomonas aeruginosa NRBC13275, as bacteria used for evaluation, was inoculated into a nutrient agar medium, cultured at 30 to 35° C. for 24 hours, and then prepared using a phosphate buffer solution to achieve $4.5 \times 10^8$ CFU/mL. The resulting solution was used as a test bacterial suspension.

The coated medical device (or medical device) to be evaluated was washed with shaking in a phosphate buffer solution five times. Then, the coated medical devices (or medical devices) were placed in sterilization containers, one each. Into each device, 2 mL of the test bacterial suspension was inoculated, and then shaken at 35° C. at 100 rpm for 2 hours. Subsequently, each coated medical device (or medical device) was washed with shaking in a phosphate buffer solution five times, and then the resulting solution together with 10 mL of a phosphate buffer solution supplemented with 0.05% by mass polysorbate 80 was placed in a Stomacher bag, and washed out with rubbing. A 10-fold dilution series of the liquid washed out was prepared using a phosphate buffer solution, and inoculated into a soybean casein digest agar medium supplemented with lecithin and polysorbate 80. Culture was performed at 30 to 35° C. for 48 to 72 hours, then the colonies formed were counted, and the number of living bacteria was calculated. The average of the N=3 values was regarded as the number of adhering living bacteria in the evaluation of the bacteria adhesion inhibiting capability.

<Moisture Content of Medical Device and Coated Medical Device>

A medical device before being used in a manufacturing method according to the present invention was immersed in a phosphate buffer solution, and left to stand at room temperature (20 to 23° C.) for 24 hours or more. Then, the medical device was pulled up from the phosphate buffer solution, the surface moisture was wiped off with a wiping cloth "Kimwipes" (registered trademark) (manufactured by Nippon Paper Crecia Co., Ltd.), and the mass (Ww) of the medical device was measured. Then, the medical device was dried at 40° C. for 2 hours in a vacuum dryer and the mass (Wd) of the medical device was measured. From these masses, the moisture content of the medical device was calculated in accordance with the following formula (1). In cases where a value obtained was less than 1%, the value was rated as not higher than the measurement limit, and denoted by "less than 1%". The average of the N=3 values was regarded as the moisture content. Also with the coated medical device obtained after the heating step, the moisture content was calculated in the same manner.

$$\text{Moisture content (\% by mass) of medical device} = 100 \times (Ww - Wd)/Ww \quad \text{Formula (1)}$$

<Rate of Change in Moisture Content of Medical Device Between Before and after Coating>

From the measurement results of the moisture contents of the medical device and the coated medical device, the rate of change in the moisture content was calculated by the following formula (2).

$$\text{Rate (\% by mass) of change in moisture content of medical device between before and after coating} = \text{moisture content (\% by mass) of coated medical device} - \text{moisture content (\% by mass) of medical device} \quad \text{Formula (2).}$$

<Coefficient of Friction>

Under the below-described conditions, the coefficient of friction of the surface of the coated medical device (or medical device) was measured at N=5, in which the surface was wet with a phosphate buffer solution. The average of the N=5 values was regarded as the coefficient of friction.

Apparatus: Friction tester KES-SE (manufactured by Kato Tech Co., Ltd.)

Friction SENS: H

Measurement SPEED: 2×1 mm/second

Friction load: 44 g

<Coefficient of Friction after 24-Hour Immersion in New Phosphate Buffer Solution (PBS) (Coefficient X of Friction)>

The sample S was provided separately, and evaluated in the same manner as in the above-described "Coefficient of Friction".

<Coefficient of Friction after 24-Hour Immersion in New Phosphate Buffer Solution (PBS) and Additional 1-Minute Scrubbing (Coefficient Y of Friction)>

The sample S was provided separately, scrubbed between the fingers (the thumb and the index finger) for 1 minute, and evaluated in the same manner as in the above-described "Coefficient of Friction".

<Amount of Lipid Adhesion>

In a 20 cc screw tube, 0.03 g of methyl palmitate, 10 g of pure water, and the coated medical device (or medical device) were placed. The screw tube was shaken for 3 hours under the conditions at 37° C. and 165 rpm. After shaking, the coated medical device (or medical device) in the screw tube was scrubbed with tap water at 40° C. and a household liquid detergent "Mama Lemon" (registered trademark) (manufactured by Lion Corporation). The sample washed was placed in a screw tube containing a phosphate buffer solution, and stored in a refrigerator at 4° C. for 24 hours. Then, the coated medical device (or medical device) was visually observed. If any turbid portion was found, the portion was rated as having methyl palmitate adhering therein, and the area of the portion having methyl palmitate adhering therein was observed with respect to the entire surface of the sample.

<Tensile Elastic Modulus>

A test piece having a width (minimum part) of 5 mm and a length of 14 mm was cut out from a coated medical device (or medical device) using a prescribed punching die. On the test piece, a tensile test was performed using Tensilon Model RTG-1210 (manufactured by A&D Company, Limited). A pulling rate was 100 mm/minute, and a grip-to-grip distance (initial) was 5 mm. A measurement was made on both the medical device before the contacting step and the heating step and the coated medical device after the contacting step and the heating step. The measurement was made at N=8, and the average of the N=6 values excluding the maximum value and the minimum value was regarded as the tensile elastic modulus.

<Rate of Change in Tensile Elastic Modulus of Medical Device Between Before and after Coating>

From the measurement results of the tensile elastic modulus, the rate of change in the tensile elastic modulus of the medical device between before and after the coating was calculated in accordance with the following formula (3).

$$\text{Rate (\%) of change in tensile elastic modulus of medical device between before and after coating} = (\text{tensile elastic modulus of coated medical device after coating} - \text{tensile elastic modulus of medical device before coating})/\text{tensile elastic modulus of medical device before coating} \times 100 \quad \text{Formula (3)}$$

<Size>

The longitudinal length of the coated medical device (or medical device) (or the diameter in the case of a circular contact lens or the like) was measured at N=3, and the average of the N=3 values was regarded as the size.

<Rate of Change in Size of Medical Device Between Before and After Coating>

From the measurement results of the size, the rate of change in the size between before and after the coating was calculated in accordance with the following formula (4).

$$\text{Rate (\%) of change in size between before and after coating} = (\text{size of coated medical device after coating} - \text{size of medical device before coating})/\text{size of medical device before coating} \times 100 \quad \text{Formula (4)}$$

<Measurement of Weight-Average Molecular Weight>

The weight-average molecular weight (hereinafter referred to as "Mw") of a polymer was measured under the following conditions.

Apparatus: Prominence GPC system (manufactured by Shimadzu Corporation)
Pump: LC-20AD
Autosampler: SIL-20AHT
Column oven: CTO-20A
Detector: RID-10A
Column: GMPWXL (manufactured by Tosoh Corporation, 7.8 mm in inner diameter×30 cm, 13 μm in particle diameter)
Solvent: water/methanol=1/1 (0.1N lithium nitrate is added)
Flow rate: 0.5 mL/minute
Measurement time: 30 minutes
Sample concentration: 0.1 to 0.3% by mass
Sample injection amount: 100 μL
Standard sample: Polyethylene oxide standard sample (manufactured by Agilent Technologies, Inc., 0.1 kD to 1258 kD)

<pH>

The pH of the solution was measured using a pH meter Eutech pH 2700 (manufactured by Eutech Instruments Pte Ltd). The "pH after the heating step" of the solution a was measured immediately after the solution a was cooled to room temperature (20 to 23° C.) after the heating step was performed.

<Thickness of Hydrophilic Polymer Layer>

The coated medical device (or medical device) was washed in a phosphate buffer solution. Then, a cross section vertical to the longitudinal direction of the frozen coated medical device (or medical device) was observed using a field-emission transmission electron microscope JEM-F200 (manufactured by JEOL Ltd.). Measurements, the positions of which were varied, were made at N=3 at an acceleration voltage of 200 kV. The average of the N=3 values was regarded as the thickness of the hydrophilic polymer layer.

Here, a measurement sample was produced by a method of $RuO_4$ staining, freezing, and ultrathin slicing.

<Elemental Composition Analysis of Hydrophilic Polymer Layer>

The form of presence of the hydrophilic polymer layer was determined by analyzing the state of the surface of the coated medical device (or medical device) in a dry state by time-of-flight secondary ion mass spectrometry.

Apparatus: TOF.SIMS5 (manufactured by ION-TOF GmbH)
Observational conditions:
Primary ion: $Bi_3^{++}$
Polarity of secondary ion: positive
Etching ion: Ar-GCIB (gas cluster ion beam)

<Phosphate Buffer Solution>

The composition of the phosphate buffer solution used in each of Examples and Comparative Examples is as follows.
KCl: 0.2 g/L
$KH_2PO_4$: 0.2 g/L
NaCl: 8.0 g/L
$Na_2HPO_4$: 1.19 g/L
EDTA2Na (disodium dihydrogen ethylenediaminetetraacetate): 0.5 g/L Example 1

As the "medical device", a commercially available silicone hydrogel lens "Acuvue Oasys" (registered trademark) (senofilcon A, manufactured by Johnson & Johnson) containing polyvinylpyrrolidone and silicone as main components was used. As the "container", a glass vial was used. As the "solution a", a solution was used, in which methoxypolyethylene glycol acrylate (with 9 polyethylene glycol chains (m=9 in the formula (II)))/N,N-dimethylacrylamide/dimethylaminopropyl acrylamide methyl chloride quaternary salt copolymer (copolymerized at a molar ratio of 4/3/3, Mw: 700,000, manufactured by Osaka Organic Chemical Industry Ltd.) was contained at 0.3% by mass as the hydrophilic polymer A in a phosphate buffer solution. The medical device was immersed in the solution a ((A) the contacting step), the glass vial was hermetically sealed with a cap ((B) the hermetically sealing step), and the medical device was heated using an autoclave at 121° C. for 30 minutes ((C) the heating step). The results of evaluating the resulting coated medical device by the above-described methods are shown in Tables 1 to 3.

Example 2

The same operation as in Example 1 was performed except that, as the solution a, a solution was used, in which solution a methoxypolyethylene glycol acrylate (with 13 polyethylene glycol chains (m=13 in the formula (II)))/N,N-dimethylacrylamide/dimethylaminopropyl acrylamide methyl chloride quaternary salt copolymer (copolymerized at a molar ratio of 4/3/3, Mw: 700,000, manufactured by Osaka Organic Chemical Industry Ltd.) was contained at 0.3% by mass in a phosphate buffer solution. The results of evaluating the resulting coated medical device by the above-described methods are shown in Tables 1 to 3.

Example 3

The same operation as in Example 1 was performed except that, as the solution a, a solution was used, in which solution a methoxypolyethylene glycol acrylate (with 13 polyethylene glycol chains)/N,N-dimethylacrylamide/dimethylaminopropyl acrylamide methyl chloride quaternary salt copolymer (copolymerized at a molar ratio of 2/1/2, Mw: 200,000, manufactured by Osaka Organic Chemical Industry Ltd.) was contained at 0.3% by mass in a phosphate buffer solution. The results of evaluating the resulting medical device by the above-described methods are shown in Tables 1 to 3.

Example 4

The same operation as in Example 1 was performed except that, as the medical device, a commercially available PF II catheter tube (manufactured by Toray Industries, Inc.) containing polyurethane as a main component was used, that, as the solution a, a solution was used, in which solution a methoxypolyethylene glycol acrylate (with 9 polyethylene glycol chains)/vinylpyrrolidone/dimethylaminopropyl acrylamide methyl chloride quaternary salt copolymer (copolymerized at a molar ratio of 2/2/1, Mw: 500,000, manufactured by Osaka Organic Chemical Industry Ltd.) was contained at 0.5% by mass in a phosphate buffer solution, and that the autoclaving conditions were performed at 90° C. for 30 minutes. The results of evaluating the resulting coated medical device by the above-described methods are shown in Tables 1 to 3.

Example 5

The same operation as in Example 4 was performed except that, as the solution a, a solution was used, in which solution a methoxypolyethylene glycol acrylate (with 9 polyethylene glycol chains)/2-hydroxyethyl methacrylate/dimethylaminopropyl acrylamide methyl chloride quaternary salt copolymer (copolymerized at a molar ratio of 2/2/1, Mw: 350,000, manufactured by Osaka Organic Chemical Industry Ltd.) was contained at 0.4% by mass in a phosphate buffer solution. The results of evaluating the resulting coated medical device by the above-described methods are shown in Tables 1 to 3.

Example 6

The same operation as in Example 1 was performed except that, as the medical device, a commercially available film "Mictron" (registered trademark) (manufactured by Toray Industries, Inc.) containing a para aromatic polyamide (aramid) as a main component was used. The results of evaluating the resulting coated medical device by the above-described methods are shown in Tables 1 to 3.

Example 7

The same operation as in Example 6 was performed except that, as the solution a, a solution was used, in which solution a methoxypolyethylene glycol acrylate (with 13 polyethylene glycol chains)/dimethylaminopropyl acrylamide methyl chloride quaternary salt copolymer (copolymerized at a molar ratio of 2/1, Mw: 500,000, manufactured by Osaka Organic Chemical Industry Ltd.) was contained at 0.5% by mass in a phosphate buffer solution. The results of evaluating the resulting coated medical device by the above-described methods are shown in Tables 1 to 3.

Example 8

The same operation was performed as in Example 1 except that, as the medical device, a commercially available hydrogel lens "MEDALIST 1 DAY PLUS" (registered trademark) (hilafilcon B, manufactured by Bausch & Lomb Incorporated) containing 2-hydroxyethyl methacrylate as a main component was used. The results of evaluating the resulting coated medical device by the above-described methods are shown in Tables 1 to 3.

Example 9

The same operation as in Example 8 was performed except that, as the solution a, a solution was used, in which solution a methoxypolyethylene glycol acrylate (with 13 polyethylene glycol chains)/N,N-dimethylacrylamide/dimethylaminopropyl acrylamide methyl chloride quaternary salt copolymer (copolymerized at a molar ratio of 2/2/1, Mw: 210,000, manufactured by Osaka Organic Chemical Industry Ltd.) was contained at 0.3% by mass in a phosphate buffer solution. The results of evaluating the resulting coated medical device by the above-described methods are shown in Tables 1 to 3.

Example 10

The same operation as in Example 1 was performed except that, as the solution a, a solution was used, in which solution a methoxypolyethylene glycol acrylate (with 9 polyethylene glycol chains)/N,N-dimethylacrylamide/dimethylaminopropyl acrylamide methyl chloride quaternary salt copolymer (copolymerized at a molar ratio of 5/3/2, Mw: 500,000, manufactured by Osaka Organic Chemical Industry Ltd.) was contained at 0.3% by mass in a phosphate buffer solution. The results of evaluating the resulting coated medical device by the above-described methods are shown in Tables 1 to 3.

Example 11

The same operation as in Example 1 was performed except that, as the solution a, a solution was used, in which solution a methoxypolyethylene glycol acrylate (with 13 polyethylene glycol chains)/vinylpyrrolidone/dimethylaminopropyl acrylamide methyl chloride quaternary salt copolymer (copolymerized at a molar ratio of 4/3/3, Mw: 600,000, manufactured by Osaka Organic Chemical Industry Ltd.) was contained at 0.3% by mass in a phosphate buffer solution. The results of evaluating the resulting coated medical device by the above-described methods are shown in Tables 1 to 3.

Example 12

The same operation as in Example 8 was performed except that, as the solution a, a solution was used, in which solution a methoxypolyethylene glycol acrylate (with 13 polyethylene glycol chains)/N,N-dimethylacrylamide/dimethylaminopropyl acrylamide methyl chloride quaternary salt copolymer (copolymerized at a molar ratio of 2/1/2, Mw: 200,000, manufactured by Osaka Organic Chemical Industry Ltd.) was contained at 0.3% by mass in a phosphate buffer solution. The results of evaluating the resulting coated medical device by the above-described methods are shown in Tables 1 to 3.

Example 13

The same operation as in Example 8 was performed except that, as the solution a, a solution was used, in which solution a methoxypolyethylene glycol acrylate (with 13 polyethylene glycol chains)/vinylpyrrolidone/dimethylaminopropyl acrylamide methyl chloride quaternary salt copolymer (copolymerized at a molar ratio of 4/3/3, Mw: 760,000, manufactured by Osaka Organic Chemical Industry Ltd.) was contained at 0.3% by mass in a phosphate buffer solution. The results of evaluating the resulting coated medical device by the above-described methods are shown in Tables 1 to 3.

TABLE 1

| | Medical Device | Moisture Content of Medical Device (% by mass) | Hydrophilic Polymer Solution | Copolymerization Ratio of Hydrophilic Polymer A compound a1/compound a2 | pH before Heating | pH after Heating |
|---|---|---|---|---|---|---|
| Example 1 | Silicone hydrogel lens | 38.0 | 0.3% by mass methoxypolyethylene glycol acrylate (with 9 polyethylene glycol chains)/N,N-dimethylacrylamide/dimethylaminopropyl acrylamide methyl chloride quaternary salt copolymer | 22/68 | 7.0 | 6.9 |
| Example 2 | Silicone hydrogel lens | 38.0 | 0.3% by mass methoxypolyethylene glycol acrylate (with 13 polyethylene glycol chains)/N,N-dimethylacrylamide/dimethylaminopropyl acrylamide methyl chloride quaternary salt copolymer | 17/74 | 7.1 | 6.8 |
| Example 3 | Silicone hydrogel lens | 38.0 | 0.3% by mass methoxypolyethylene glycol acrylate (with 13 polyethylene glycol chains)/N,N-dimethylacrylamide/dimethylaminopropyl acrylamide methyl chloride quaternary salt copolymer | 23/72 | 7.1 | 6.8 |
| Example 4 | PF II catheter tube | <1.0 | 0.5% by mass methoxypolyethylene glycol acrylate (with 9 polyethylene glycol chains)/vinylpyrrolidone/dimethylaminopropyl acrylamide methyl chloride quaternary salt copolymer | 15/69 | 7.0 | 6.8 |
| Example 5 | PF II catheter tube | <1.0 | 0.4% by mass methoxypolyethylene glycol acrylate (with 9 polyethylene glycol chains)/2-hydroxyethyl methacrylate/dimethylaminopropyl acrylamide methyl chloride quaternary salt copolymer | 14/67 | 7.1 | 6.8 |
| Example 6 | Aramid film | <1.0 | 0.3% by mass methoxypolyethylene glycol acrylate (with 9 polyethylene glycol chains)/N,N-dimethylacrylamide/dimethylaminopropyl acrylamide methyl chloride quaternary salt copolymer | 22/68 | 7.1 | 6.8 |
| Example 7 | Aramid film | <1.0 | 0.5% by mass methoxypolyethylene glycol acrylate (with 13 polyethylene glycol chains)/dimethylaminopropyl acrylamide methyl chloride quaternary salt copolymer | 14/86 | 7.1 | 6.8 |
| Example 8 | Hydrogel lens | 59.0 | 0.3% by mass methoxypolyethylene glycol acrylate (with 9 polyethylene glycol chains)/N,N-dimethylacrylamide/dimethylaminopropyl acrylamide methyl chloride quaternary salt copolymer | 22/68 | 7.1 | 6.8 |
| Example 9 | Hydrogel lens | 59.0 | 0.3% by mass methoxypolyethylene glycol acrylate (with 13 polyethylene glycol chains)/N,N-dimethylacrylamide/dimethylaminopropyl acrylamide methyl chloride quaternary salt copolymer | 12/76 | 7.1 | 6.9 |
| Example 10 | Silicone hydrogel lens | 38.0 | 0.3% by mass methoxypolyethylene glycol acrylate (with 9 polyethylene glycol chains)/N,N-dimethylacrylamide/dimethylaminopropyl acrylamide methyl chloride quaternary salt copolymer | 13/77 | 7.1 | 6.8 |
| Example 11 | Silicone hydrogel lens | 38.0 | 0.3% by mass methoxypolyethylene glycol acrylate (with 13 polyethylene glycol chains)/vinylpyrrolidone/dimethylaminopropyl acrylamide methyl chloride quaternary salt copolymer | 17/73 | 7.1 | 6.8 |
| Example 12 | Hydrogel lens | 59.0 | 0.3% by mass methoxypolyethylene glycol acrylate (with 13 polyethylene glycol chains)/N,N-dimethylacrylamide/dimethylaminopropyl acrylamide methyl chloride quaternary salt copolymer | 23/72 | 7.1 | 7.0 |
| Example 13 | Hydrogel lens | 59.0 | 0.3% by mass methoxypolyethylene glycol acrylate (with 13 polyethylene glycol chains)/vinylpyrrolidone/dimethylaminopropyl acrylamide methyl chloride quaternary salt copolymer | 17/73 | 7.1 | 7.0 |

TABLE 2

|  | Liquid Film Retention Time (second) | Liquid Film Retention Time after 24 Hours (second) | Contact Angle of Droplet (°) | Contact Angle X of Droplet (°) | Contact Angle Y of Droplet | Number of Adhering Living Bacteria (CFU) | Moisture Content of Coated Medical Device (% by mass) |
|---|---|---|---|---|---|---|---|
| Example 1 | A (120 seconds) | A (120 seconds) | 26 | 101 | 100 | $1.1 \times 10^5$ | 38.1 |
| Example 2 | A (120 seconds) | A (120 seconds) | 23 | 100 | 99 | $1.5 \times 10^5$ | 38.4 |
| Example 3 | A (120 seconds) | A (120 seconds) | 28 | 101 | 100 | $1.2 \times 10^5$ | 38.3 |
| Example 4 | A (20 seconds) | B (15 seconds) | Unmeasurable owing to tubular shape | | | | 0.5 |
| Example 5 | A (20 seconds) | B (15 seconds) | Unmeasurable owing to tubular shape | | | | 0.7 |
| Example 6 | A (20 seconds) | B (15 seconds) | Unmeasurable owing to sheet-like shape | | | Not evaluated | 0.5 |
| Example 7 | A (20 seconds) | B (18 seconds) | Unmeasurable owing to sheet-like shape | | | Not evaluated | 0.4 |
| Example 8 | A (120 seconds) | A (30 seconds) | 57 | 60 | 57 | $4.1 \times 10^5$ | 59.2 |
| Example 9 | A (120 seconds) | A (20 seconds) | 56 | 59 | 52 | $6.9 \times 10^5$ | 59.3 |
| Example 10 | A (120 seconds) | A (120 seconds) | 28 | 100 | 98 | $7.1 \times 10^4$ | 38.5 |
| Example 11 | A (120 seconds) | A (120 seconds) | 29 | 99 | 100 | $6.8 \times 10^4$ | 38.6 |
| Example 12 | A (120 seconds) | A (30 seconds) | 57 | 62 | 58 | $6.8 \times 10^5$ | 59.3 |
| Example 13 | A (120 seconds) | A (25 seconds) | 48 | 59 | 57 | $4.0 \times 10^5$ | 59.3 |

|  | Thickness of Hydrophilic Polymer Layer (nm) | Form of Presence of Hydrophilic Polymer Layer | Rate of Change in Moisture Content (% by mass) | Coefficient of Friction | Coefficient X of Friction | Coefficient Y of Friction |
|---|---|---|---|---|---|---|
| Example 1 | 40 | Two-layer structure of single layer and mixed layer | 0.1 | 0.073 | 0.161 | 0.301 |
| Example 2 | 45 | Two-layer structure of single layer and mixed layer | 0.4 | 0.079 | 0.172 | 0.309 |
| Example 3 | 41 | Two-layer structure of single layer and mixed layer | 0.3 | 0.066 | 0.200 | 0.313 |
| Example 4 | 15 | Two-layer structure of single layer and mixed layer | 0.5 | Unmeasurable owing to tubular shape | | |
| Example 5 | 18 | Two-layer structure of single layer and mixed layer | 0.7 | Unmeasurable owing to tubular shape | | |
| Example 6 | 17 | Two-layer structure of single layer and mixed layer | 0.5 | Unmeasurable owing to sheet-like shape | | |
| Example 7 | 12 | Two-layer structure of single layer and mixed layer | 0.4 | Unmeasurable owing to sheet-like shape | | |
| Example 8 | 38 | Only mixed layer | 0.2 | 0.016 | 0.045 | 0.030 |
| Example 9 | 35 | Only mixed layer | 0.3 | 0.010 | 0.039 | 0.040 |
| Example 10 | 35 | Two-layer structure of single layer and mixed layer | 0.5 | 0.036 | 0.201 | 0.309 |
| Example 11 | 41 | Two-layer structure of single layer and mixed layer | 0.6 | 0.032 | 0.215 | 0.314 |
| Example 12 | 34 | Only mixed layer | 0.3 | 0.045 | 0.052 | 0.059 |
| Example 13 | 36 | Only mixed layer | 0.3 | 0.049 | 0.071 | 0.069 |

TABLE 3

|  | Amount of Lipid Adhesion | Tensile Elastic Modulus of Medical Device (MPa) | Tensile Elastic Modulus of Coated Medical Device (MPa) | Rate of Change in tensile Elastic Modulus (%) | Size of Medical Device (mm) | Size of Coated Medical Device (mm) | Rate of Change in Size (%) |
|---|---|---|---|---|---|---|---|
| Example 1 | No adhesion | 0.70 | 0.69 | −1.40 | 14.20 | 14.19 | −0.07 |
| Example 2 | No adhesion | 0.70 | 0.71 | 1.40 | 14.20 | 14.18 | −0.14 |
| Example 3 | No adhesion | 0.70 | 0.72 | 2.90 | 14.20 | 14.21 | 0.07 |
| Example 4 | No adhesion | Unmeasurable owing to tubular shape | | | | | |
| Example 5 | No adhesion | Unmeasurable owing to tubular shape | | | | | |
| Example 6 | No adhesion | 1.10 | 1.15 | 4.50 | 15.00 | 15.05 | 0.33 |
| Example 7 | No adhesion | 1.10 | 1.15 | 4.50 | 15.00 | 15.08 | 0.53 |
| Example 8 | No adhesion | 0.26 | 0.27 | 3.80 | 14.20 | 14.18 | −0.14 |
| Example 9 | No adhesion | 0.26 | 0.27 | 3.80 | 14.20 | 14.19 | −0.07 |
| Example 10 | No adhesion | 0.70 | 0.71 | 1.40 | 14.20 | 14.21 | 0.07 |
| Example 11 | No adhesion | 0.70 | 0.69 | −1.40 | 14.20 | 14.21 | 0.07 |
| Example 12 | No adhesion | 0.26 | 0.27 | 3.80 | 14.20 | 14.19 | −0.07 |
| Example 13 | No adhesion | 0.26 | 0.27 | 3.80 | 14.20 | 14.19 | −0.07 |

Comparative Example 1

The same operation as in Example 1 was performed except that, in place of the solution a, a solution was used, in which solution an acrylic acid/vinylpyrrolidone/N,N-dimethylacrylamide copolymer (copolymerized at a molar ratio of 1/1/2, Mw: 550,000, manufactured by Osaka Organic Chemical Industry Ltd.) was contained at 0.2% by mass in a phosphate buffer solution. The results of evaluating the resulting coated medical device (no hydrophilic polymer layer was identified) by the above-described methods are shown in Tables 4 to 6.

Comparative Example 2

The same operation as in Example 1 was performed except that, in place of the solution a, a solution was used, in which solution an acrylic acid/vinylpyrrolidone/N,N-dimethylacrylamide copolymer (copolymerized at a molar ratio of 1/1/2, Mw: 330,000, manufactured by Osaka Organic Chemical Industry Ltd.) was contained at 0.1% by mass in a phosphate buffer solution. The results of evaluating the resulting coated medical device (no hydrophilic polymer layer was identified) by the above-described methods are shown in Tables 4 to 6.

Comparative Example 3

The same operation as in Example 1 was performed except that, in place of the solution a, a solution was used, in which solution an acrylic acid/N,N-dimethylacrylamide copolymer (copolymerized at a molar ratio of 1/9, Mw: 300,000, manufactured by Osaka Organic Chemical Industry Ltd.) was contained at 0.1% by mass in a phosphate buffer solution. The results of evaluating the resulting coated medical device (no hydrophilic polymer layer was identified) by the above-described methods are shown in Tables 4 to 6.

Comparative Example 4

The same operation as in Example 1 was performed except that, in place of the solution a, a solution was used, in which solution an acrylic acid/methoxypolyethylene glycol acrylate (with 9 polyethylene glycol chains)/N,N-dimethylacrylamide copolymer (copolymerized at a molar ratio of 1/1/8, Mw: 400,000, manufactured by Osaka Organic Chemical Industry Ltd.) was contained at 0.2% by mass in a phosphate buffer solution. The results of evaluating the resulting coated medical device (no hydrophilic polymer layer was identified) by the above-described methods are shown in Tables 4 to 6.

Comparative Example 5

The same operation as in Example 1 was performed except that, in place of the solution a, a solution was used, in which solution an acrylic acid/vinylpyrrolidone copolymer (copolymerized at a molar ratio of 1/4, Mw: 590,000, manufactured by Osaka Organic Chemical Industry Ltd.) was contained at 0.1% by mass in a phosphate buffer solution. The results of evaluating the resulting coated medical device (no hydrophilic polymer layer was identified) by the above-described methods are shown in Tables 4 to 6.

Comparative Example 6

The same operation as in Example 1 was performed except that, in place of the solution a, a solution was used, in which solution an acrylic acid/vinylpyrrolidone copolymer (copolymerized at a molar ratio of 1/9, Mw: 390,000, manufactured by Osaka Organic Chemical Industry Ltd.) was contained at 0.1% by mass in a phosphate buffer solution. The results of evaluating the resulting coated medical device (no hydrophilic polymer layer was identified) by the above-described methods are shown in Tables 4 to 6.

Comparative Example 7

The same operation as in Example 1 was performed except that, in place of the solution a, a solution was used, in which solution an acrylic acid/2-hydroxyethyl methacrylate/N,N-dimethylacrylamide copolymer (copolymerized at a molar ratio of 1/1/2, Mw: 430,000, manufactured by Osaka Organic Chemical Industry Ltd.) was contained at 0.2% by mass in a phosphate buffer solution. The results of evaluating the resulting coated medical device (no hydrophilic polymer layer was identified) by the above-described methods are shown in Tables 4 to 6.

Comparative Example 8

The same operation as in Example 1 was performed except that, in place of the solution a, a solution was used, in which solution an acrylic acid/2-hydroxyethyl methacrylate/N,N-dimethylacrylamide copolymer (copolymerized at a molar ratio of 1/1/8, Mw: 480,000, manufactured by Osaka Organic Chemical Industry Ltd.) was contained at 0.2% by mass in a phosphate buffer solution. The results of evaluating the resulting coated medical device (no hydrophilic polymer layer was identified) by the above-described methods are shown in Tables 4 to 6.

Comparative Example 9

The same operation as in Example 1 was performed except that, in place of the solution a, a solution was used, in which solution polyvinylpyrrolidone (Mw: 500,000, manufactured by Osaka Organic Chemical Industry Ltd.) was contained at 0.3% by mass in a phosphate buffer solution. The results of evaluating the resulting coated medical device (no hydrophilic polymer layer was identified) by the above-described methods are shown in Tables 4 to 6.

Comparative Example 10

The same operation as in Example 1 was performed except that, in place of the solution a, a solution was used, in which solution poly(N,N-dimethylacrylamide) (Mw: 700,000, manufactured by Osaka Organic Chemical Industry Ltd.) was contained at 0.3% by mass in a phosphate buffer solution. The results of evaluating the resulting coated medical device (no hydrophilic polymer layer was identified) by the above-described methods are shown in Tables 4 to 6.

Comparative Example 11

The same operation as in Example 1 was performed except that, in place of the solution a, a phosphate buffer solution was used. The results of evaluating the resulting medical device (no polymer layer was identified) by the above-described methods are shown in Tables 4 to 6.

Comparative Example 12

The same operation was performed as in Comparative Example 11 except that, as the medical device, a commercially available hydrogel lens "MEDALIST 1 DAY PLUS" (registered trademark) (hilafilcon B, manufactured by Bausch & Lomb Incorporated) containing 2-hydroxyethyl methacrylate as a main component was used. The results of evaluating the resulting medical device (no polymer layer was identified) by the above-described methods are shown in Tables 4 to 6.

Comparative Example 13

The same operation as in Comparative Example 11 was performed except that, as the medical device, a commercially available PFII catheter tube (manufactured by Toray Industries, Inc.) containing polyurethane as a main component was used. The results of evaluating the resulting medical device (no polymer layer was identified) by the above-described methods are shown in Tables 4 to 6.

Comparative Example 14

The same operation as in Comparative Example 11 was performed except that, as the medical device, a commercially available film "Mictron" (registered trademark) (manufactured by Toray Industries, Inc.) containing a para aromatic polyamide (aramid) as a main component was used. The results of evaluating the resulting medical device (no hydrophilic polymer layer was identified) by the above-described methods are shown in Tables 4 to 6.

Comparative Example 15

The same operation was performed as in Comparative Example 10 except that, as the medical device, a commercially available hydrogel lens "MEDALIST 1 DAY PLUS" (registered trademark) (hilafilcon B, manufactured by Bausch & Lomb Incorporated) containing 2-hydroxyethyl methacrylate as a main component was used. The results of evaluating the resulting medical device (no polymer layer was identified) by the above-described methods are shown in Tables 4 to 6.

TABLE 4

| | Base Material | Moisture Content of Medical Device (% by mass) | Hydrophilic Polymer Solution | Copolymerization Ratio of Hydrophilic Polymer A compound a1/ compound a2 | pH before Heating | pH after Heating |
|---|---|---|---|---|---|---|
| Comparative Example 1 | Silicone hydrogel lens | 38.0 | 0.2% by mass acrylic acid/vinylpyrrolidone/ N,N-dimethylacrylamide copolymer | 0/0 | 7.0 | 7.0 |
| Comparative Example 2 | Silicone hydrogel lens | 38.0 | 0.1% by mass acrylic acid/vinylpyrrolidone/ N,N-dimethylacrylamide copolymer | 0/0 | 7.0 | 7.1 |
| Comparative Example 3 | Silicone hydrogel lens | 38.0 | 0.1% by mass acrylic acid/ N,N-dimethylacrylamide copolymer | 0/0 | 6.9 | 7.0 |
| Comparative Example 4 | Silicone hydrogel lens | 38.0 | 0.2% by mass acrylic acid/methoxy-polyethylene glycol acrylate (with 9 polyethylene glycol chains)/ N,N-dimethylacrylamide copolymer | 0/36 | 6.9 | 6.9 |
| Comparative Example 5 | Silicone hydrogel lens | 38.0 | 0.1% by mass acrylic acid/vinylpyrrolidone copolymer | 0/0 | 6.9 | 7.0 |
| Comparative Example 6 | Silicone hydrogel lens | 38.0 | 0.1% by mass acrylic acid/vinylpyrrolidone copolymer | 0/0 | 6.9 | 7.0 |
| Comparative Example 7 | Silicone hydrogel lens | 38.0 | 0.2% by mass acrylic acid/2-hydroxyethyl methacrylate/ N,N-dimethylacrylamide copolymer | 0/0 | 6.8 | 6.9 |
| Comparative Example 8 | Silicone hydrogel lens | 38.0 | 0.2% by mass acrylic acid/2-hydroxyethyl methacrylate/ N,N-dimethylacrylamide copolymer | 0/0 | 7.0 | 7.1 |
| Comparative Example 9 | Silicone hydrogel lens | 38.0 | 0.3% by mass polyvinylpyrrolidone | 0/0 | 7.0 | 7.1 |
| Comparative Example 10 | Silicone hydrogel lens | 38.0 | 0.3% by mass poly(N,N-dimethylacrylamide) | 0/0 | 7.1 | 7.2 |
| Comparative Example 11 | Silicone hydrogel lens | 38.0 | None | None | 7.0 | 7.2 |
| Comparative Example 12 | Hydrogel lens | 59.0 | None | None | 7.0 | 7.1 |
| Comparative Example 13 | PF II catheter tube | <1.0 | None | None | 7.0 | 7.1 |
| Comparative Example 14 | Aramid film | <1.0 | None | None | 7.0 | 7.1 |
| Comparative Example 15 | Hydrogel lens | 59.0 | 0.3% by mass poly(N,N-dimethylacrylamide) | 0/0 | 7.1 | 7.2 |

TABLE 5

| | Liquid Film Retention Time (second) | Liquid Film Retention Time after 24 Hours (second) | Contact Angle of Droplet (°) | Contact Angle X of Droplet (°) | Contact Angle Y of Droplet (°) | Number of Adhering Living Bacteria (CFU) | Moisture Content of Coated Medical Device (% by mass) |
|---|---|---|---|---|---|---|---|
| Comparative Example 1 | D (1 second) | D (1 second) | 100 | 101 | 103 | $6.9 \times 10^6$ | 38.0 |
| Comparative Example 2 | D (1 second) | D (1 second) | 102 | 104 | 102 | $8.1 \times 10^6$ | 38.0 |
| Comparative Example 3 | D (1 second) | D (1 second) | 101 | 103 | 100 | $9.1 \times 10^6$ | 38.0 |
| Comparative Example 4 | D (1 second) | D (1 second) | 103 | 100 | 102 | $8.5 \times 10^6$ | 38.0 |
| Comparative Example 5 | D (1 second) | D (1 second) | 104 | 106 | 101 | $9.5 \times 10^6$ | 38.0 |
| Comparative Example 6 | D (1 second) | D (1 second) | 103 | 105 | 101 | $7.8 \times 10^6$ | 38.0 |
| Comparative Example 7 | D (1 second) | D (1 second) | 101 | 104 | 102 | $8.1 \times 10^6$ | 38.0 |
| Comparative Example 8 | D (1 seconds) | D (1 seconds) | 105 | 106 | 108 | $8.9 \times 10^6$ | 38.0 |
| Comparative Example 9 | A (120 seconds) | D (4 seconds) | 40 | 99 | 103 | $7.7 \times 10^6$ | 38.0 |
| Comparative Example 10 | A (120 seconds) | D (4 seconds) | 42 | 98 | 105 | $7.5 \times 10^6$ | 38.0 |
| Comparative Example 11 | D (7 seconds) | D (5 seconds) | 103 | 107 | 103 | $9.0 \times 10^6$ | 38.0 |
| Comparative Example 12 | D (9 seconds) | D (9 seconds) | 72 | 77 | 75 | $9.2 \times 10^6$ | 59.0 |
| Comparative Example 13 | E (less than 1 second) | E (less than 1 second) | Unmeasurable owing to tubular shape | | | | <1 |
| Comparative Example 14 | E (less than 1 second) | E (less than 1 second) | Unmeasurable owing to sheet-like shape | | | Not evaluated | <1 |
| Comparative Example 15 | A (120 seconds) | D (3 seconds) | 57 | 75 | 78 | $9.0 \times 10^6$ | 59.0 |

| | Thickness of Hydrophilic Polymer Layer (nm) | Form of Presence of Hydrophilic Polymer Layer | Rate of Change in Moisture Content (% by mass) | Coefficient of Friction | Coefficient X of Friction | Coefficient Y of Friction |
|---|---|---|---|---|---|---|
| Comparative Example 1 | 0 | No layer identified | 0 | 0.250 | 0.340 | 0.339 |
| Comparative Example 2 | 0 | No layer identified | 0 | 0.248 | 0.342 | 0.346 |
| Comparative Example 3 | 0 | No layer identified | 0 | 0.251 | 0.349 | 0.341 |
| Comparative Example 4 | 0 | No layer identified | 0 | 0.249 | 0.345 | 0.349 |
| Comparative Example 5 | 0 | No layer identified | 0 | 0.254 | 0.348 | 0.341 |
| Comparative Example 6 | 0 | No layer identified | 0 | 0.261 | 0.339 | 0.343 |
| Comparative Example 7 | 0 | No layer identified | 0 | 0.262 | 0.345 | 0.350 |
| Comparative Example 8 | 0 | No layer identified | 0 | 0.259 | 0.351 | 0.347 |
| Comparative Example 9 | 0 | No layer identified | 0 | 0.123 | 0.325 | 0.340 |
| Comparative Example 10 | 0 | No layer identified | 0 | 0.110 | 0.350 | 0.318 |
| Comparative Example 11 | 0 | No layer identified | 0 | 0.340 | 0.330 | 0.341 |
| Comparative Example 12 | 0 | No layer identified | 0 | 0.350 | 0.348 | 0.351 |
| Comparative Example 13 | 0 | No layer identified | 0 | Unmeasurable owing to tubular shape | | |
| Comparative Example 14 | 0 | No layer identified | 0 | Unmeasurable owing to sheet-like shape | | |
| Comparative Example 15 | 0 | No layer identified | 0 | 0.124 | 0.349 | 0.353 |

TABLE 6

|  | Amount of Lipid Adhesion | Tensile Elastic Modulus of Medical Device (MPa) | Coated Tensile Elastic Modulus of Medical Device (MPa) | Rate of Change in Tensile Elastic Modulus (%) | Size of Medical Device (mm) | Size of Coated Medical Device (mm) | Rate of Change in Size (%) |
|---|---|---|---|---|---|---|---|
| Comparative Example 1 | Adhesion on 20% of whole area | 0.71 | 0.72 | 1.40 | 14.20 | 14.21 | 0.07 |
| Comparative Example 2 | Adhesion on 20% of whole area | 0.71 | 0.71 | 0.56 | 14.20 | 14.21 | 0.07 |
| Comparative Example 3 | Adhesion on 20% of whole area | 0.71 | 0.70 | −1.40 | 14.20 | 14.19 | −0.07 |
| Comparative Example 4 | Adhesion on 20% of whole area | 0.71 | 0.71 | 0.16 | 14.20 | 14.21 | 0.07 |
| Comparative Example 5 | Adhesion on 20% of whole area | 0.71 | 0.71 | 0.56 | 14.20 | 14.20 | 0.04 |
| Comparative Example 6 | Adhesion on 20% of whole area | 0.71 | 0.70 | −2.40 | 14.20 | 14.20 | 0.04 |
| Comparative Example 7 | Adhesion on 20% of whole area | 0.71 | 0.70 | −1.10 | 14.20 | 14.19 | −0.07 |
| Comparative Example 8 | Adhesion on 20% of whole area | 0.71 | 0.71 | 0.80 | 14.20 | 14.21 | 0.07 |
| Comparative Example 9 | Adhesion on 20% of whole area | 0.71 | 0.71 | 0.90 | 14.20 | 14.21 | 0.07 |
| Comparative Example 10 | Adhesion on 20% of whole area | 0.71 | 0.71 | 0.70 | 14.20 | 14.21 | 0.07 |
| Comparative Example 11 | Adhesion on 20% of whole area | 0.71 | 0.71 | 0.00 | 14.20 | 14.20 | 0.00 |
| Comparative Example 12 | No adhesion | 0.26 | 0.26 | 0.00 | 14.20 | 14.20 | 0.00 |
| Comparative Example 13 | Adhesion on whole surface | Unmeasurable owing to tubular shape | | | | | |
| Comparative Example 14 | Adhesion on whole surface | 1.10 | 1.10 | 0.00 | 15.00 | 15.00 | 0.00 |
| Comparative Example 15 | No adhesion | 0.26 | 0.26 | 0.00 | 14.20 | 14.21 | 0.07 |

From the comparison of the results between Examples and Comparative Examples, it is evident that the present invention can provide a medical device with not only sufficient hydrophilicity and lubricity but also an excellent bacteria adhesion inhibiting capability.

In addition, in cases where attention is paid to changes caused by scrubbing in the contact angle of a droplet and in the coefficient of friction, that is, a difference between the contact angle X of a droplet and the contact angle Y of a droplet and a difference between the coefficient X of friction and the coefficient Y of friction, it can be said that a system in which the rate of change was smaller allowed a hydrophilic polymer layer having a higher adsorptive force and an excellent durability to be formed on the surface of the medical device. The results of Examples 8, 9, 12 and 13 match this consequence.

The invention claimed is:

1. A method for manufacturing a coated medical device, comprising:

(A) a contacting step of housing a medical device in a container, and bringing said medical device into contact with a solution a containing a hydrophilic polymer A; and (C) a heating step of heating said container; wherein said hydrophilic polymer A is a polymer containing, as a monomer unit, a compound a1 having a quaternary ammonium cation group represented by the following general formula (I):

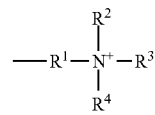

wherein, in the general formula (I), $R^1$ represents an optionally substituted $C_{1-20}$ divalent organic group; and $R^2$ to $R^4$ each independently represent a $C_{1-16}$ alkyl group or a $C_{6-18}$ aryl group;

wherein said hydrophilic polymer A further contains, as a monomer unit, a compound a2 having a structure represented by the following general formula (II):

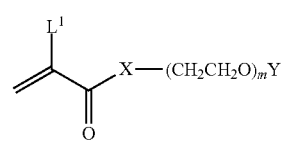

wherein, in the general formula (II), $L^1$ represents a hydrogen atom or a methyl group; X represents an oxygen atom or $NA^2$, wherein $A^2$ represents a hydrogen atom or an alkyl group; m represents an integer of 1 to 30; and Y represents methyl group, ethyl group, propyl group, isopropyl group, or butyl group;

wherein, with respect to 100% by mass of the whole hydrophilic polymer A, a content of the compound a1 is 5% by mass or more and 90% by mass or less, and a content of the compound a2 is 10% by mass or more and 80% by mass or less; and wherein the pH of the solution a after said heating step is 6.1 to 8.0.

2. The method for manufacturing said coated medical device according to claim 1, further comprising (B) a hermetically sealing step of hermetically sealing said container in which said medical device is housed.

3. The method for manufacturing a coated medical device according to claim 1, wherein said hydrophilic polymer A comprises an amide group.

4. The method for manufacturing a coated medical device according to claim 1, wherein said medical device is sterilized by said heating step.

5. The method for manufacturing a coated medical device according to claim 1, wherein said medical device comprises a material selected from the group consisting of a hydrogel, a silicone hydrogel, a low water content soft material, and a low water content hard material.

6. The method for manufacturing a coated medical device according to claim 5, wherein said hydrogel is selected from the group consisting of tefilcon, tetrafilcon, helfilcon, mafilcon, polymacon, hioxifilcon, alfafilcon, omafilcon, nelfilcon, nesofilcon, hilafilcon, acofilcon, deltafilcon, etafilcon, focofilcon, ocufilcon, phemfilcon, methafilcon, and vilfilcon.

7. The method for manufacturing a coated medical device according to claim 5, wherein said silicone hydrogel is selected from the group consisting of lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon.

8. The method for manufacturing a coated medical device according to claim 5, wherein said low water content soft material and/or said low water content hard material is/are selected from the group consisting of polysulfone, polystyrene, polymethyl methacrylate, polyurethane, and polyamide.

9. The method for manufacturing a coated medical device according to claim 1, wherein said medical device is selected from the group consisting of an ophthalmic lens, a dermal covering material, a wound dressing material, a skin protection material, a skin medicine carrier, an infusion tube, a gas delivery tube, a drainage tube, a blood circuit, a covering tube, a catheter, a stent, a sheath, a biosensor chip, artificial heart and lung, and an endoscopic covering material.

10. The method for manufacturing a coated medical device according to claim 9, wherein said ophthalmic lens is a contact lens.

* * * * *